(12) United States Patent
Li et al.

(10) Patent No.: US 9,699,859 B1
(45) Date of Patent: Jul. 4, 2017

(54) CONFIGURATION OF AN AUTOMATED PERSONAL FITNESS COACHING DEVICE

(71) Applicant: Moov Inc., Mountain View, CA (US)

(72) Inventors: Meng Li, Mountain View, CA (US);
Yaohua Hu, Mountain View, CA (US);
Tong Yuan, Beijing (CN)

(73) Assignee: Moov Inc., San Mateo, CA (US)

( * ) Notice: Subject to any disclaimer, the term of this patent is extended or adjusted under 35 U.S.C. 154(b) by 10 days.

(21) Appl. No.: 14/814,092

(22) Filed: Jul. 30, 2015

Related U.S. Application Data

(60) Provisional application No. 62/032,271, filed on Aug. 1, 2014.

(51) Int. Cl.
*H05B 33/08* (2006.01)
*A63B 24/00* (2006.01)

(52) U.S. Cl.
CPC ..... *H05B 33/0872* (2013.01); *A63B 24/0062* (2013.01); *A63B 24/0075* (2013.01); *A63B 2220/34* (2013.01); *A63B 2220/40* (2013.01)

(58) Field of Classification Search
CPC ............ H05B 37/0227; H05B 37/0245; H05B 37/0272; Y02B 20/40; Y02B 20/44; Y02B 20/48; G06F 1/163; G06F 11/0709; G06F 3/04847; G06F 3/0304; G06F 3/04817; G06F 3/04886; A61B 5/742; A61B 5/681; A63B 24/0062; A63B 24/0075; A63B 2071/0675; A63B 2071/0683
See application file for complete search history.

(56) References Cited

U.S. PATENT DOCUMENTS

| | | | | |
|---|---|---|---|---|
| 8,172,724 | B2 * | 5/2012 | Solomon ............ | A63B 24/0062 482/1 |
| 8,396,608 | B2 * | 3/2013 | Subbloie ................... | G06F 1/28 370/452 |
| 8,570,273 | B1 * | 10/2013 | Smith .................... | G06F 3/0338 345/156 |
| 8,729,834 | B1 * | 5/2014 | Funderburk ....... | H05B 37/0227 315/312 |
| 9,241,124 | B2 * | 1/2016 | Athavale ................. | G06F 3/011 |
| 9,259,180 | B2 * | 2/2016 | McCaffrey ............ | A61B 5/486 |
| 9,308,417 | B2 * | 4/2016 | Grundy ............. | A63B 24/0062 |
| 9,354,778 | B2 * | 5/2016 | Cornaby ............. | G06F 3/04847 |

* cited by examiner

*Primary Examiner* — Haissa Philogene
(74) *Attorney, Agent, or Firm* — Van Pelt, Yi & James LLP

(57) ABSTRACT

An automated fitness coaching device is presented, comprising: a light emitting diode (LED); a set of one or more sensors configured to obtain motion data samples; one or more processors coupled to the LED and the set of one or more sensors; wherein the one or more processors are configured to: obtain an indication of a color configuration; and cause a control signal to be sent to the LED to cause the LED to emit a color according to the color configuration.

23 Claims, 8 Drawing Sheets

US 9,699,859 B1

CONFIGURATION OF AN AUTOMATED PERSONAL FITNESS COACHING DEVICE

CROSS REFERENCE TO OTHER APPLICATIONS

This application claims priority to U.S. Provisional Patent Application No. 62/032,271 entitled CONFIGURATION OF AN AUTOMATED PERSONAL FITNESS COACHING DEVICE filed Aug. 1, 2014 which is incorporated herein by reference for all purposes.

BACKGROUND OF THE INVENTION

Conventional ways of exercising to achieve fitness goals can be challenging for many people. Exercising typically involves performing repetitive motions, which many view as tedious and therefore not enjoyable. Moreover, it is difficult for individuals to track the performance of their exercises besides using basic measurements such as time and distance. Today, one often needs to hire a personal trainer to get deeper knowledge and advice about one's workouts. In addition to the high cost, the expertise of the personal trainers can vary and the quality of their advice cannot be guaranteed.

Wearable fitness devices have been gaining popularity in recent years. There are some wearable devices that provide functions such as automatic step counting or distance tracking. These devices, however, typically only provide limited information about basic exercises such as how much a person has walked in a day, which can be insufficient for those who want to improve the quality of their workouts in addition to quantity.

For a wearable fitness device to provide more sophisticated functions such as personal fitness coaching, the device must first be configured. Because a user may use multiple such devices (e.g., wear multiple devices on arms and legs during an exercise session to monitor form), a way to configure the devices so that the user may distinguish among multiple devices is needed. Moreover, if a user uses multiple management devices to manage the wearable fitness device (e.g., using his smartphone as well as tablet to manage the wearable fitness device throughout the day), the configuration should accommodate this scenario. The configuration process should also be intuitive for the user.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The configuration of an automated personal fitness coaching system is described. In some embodiments, a sensor device includes a light emitting diode (LED), a set of one or more sensors configured to obtain motion data samples, and one or more processors coupled to the LED and the set of sensors. The one or more processors are configured to obtain an indication of a color configuration and cause a control signal to be sent to the LED to cause the LED to emit a color according to the color configuration. Different sensor devices can be configured with different colors so the user can distinguish individual devices. In some embodiments, the sensor device communicates with a management device which performs management and processing functions.

Figure 1:
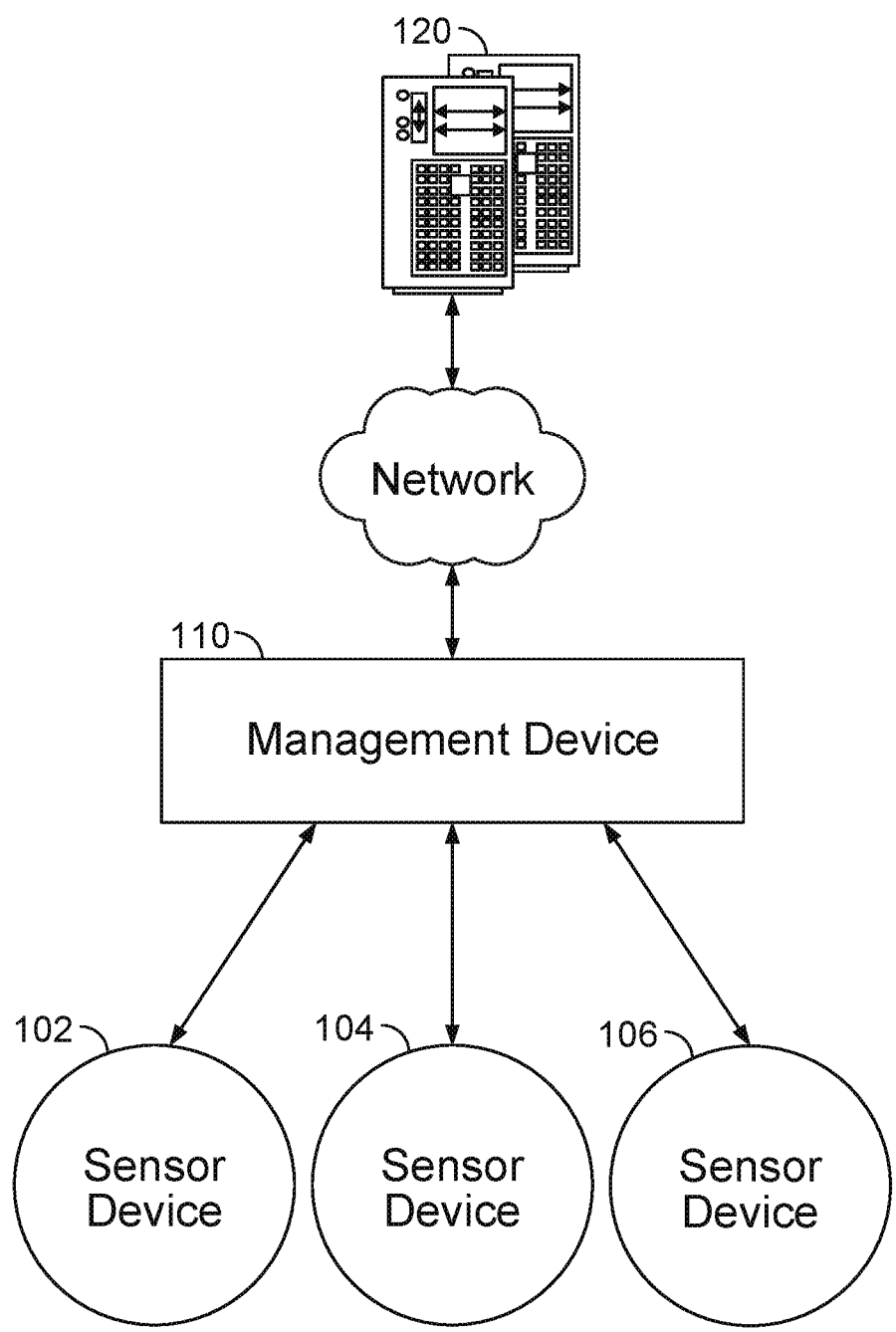
FIG. 1 is a system diagram illustrating an embodiment of an automated fitness coaching system.

FIG. 1 is a system diagram illustrating an embodiment of an automated fitness coaching system. In this example, one or more sensor devices 102-106 (also referred to as personal fitness coaching devices) are used to detect motion. As will be described in greater detail below, a sensor device includes one or more accelerometers, one or more gyroscopes, and optionally one or more magnetometers that are configured to take measurement data samples of acceleration, angular velocity, and optionally magnetic field, respectively, in connection with the motions of the device. A user wears one or more sensor device(s) during exercises (e.g., on the ankle while running, on arms and legs while swimming, etc.) to capture the user's motion data.

The data samples are processed to evaluate the user's performance and optionally provide feedback. In some embodiments, a sensor device includes a processor configured to perform the data processing, evaluation, and/or feedback. In some embodiments, the configurations of the sensor device such as the LED color are also determined based on the data samples. The processing techniques are described in the section below entitled "Processing Techniques."

In some embodiments such as the example shown, the sensor devices are connected (e.g., via a wireless communication interface such as Bluetooth interface) to a management device 110, which can be a personal computer, a smartphone, a tablet, or any other appropriate computing device that is configured to perform the data processing, evaluation, and/or feedback. The management device executes one or more configurations and other related management applications to manage the configuration and operations of the sensor devices. In some embodiments, the management functions are performed by the sensor device directly.

In some embodiments, the management device (or the sensor device if the sensor device directly performs processing) is optionally connected to one or more cloud-based devices 120 via a network such as the Internet. Devices 120 (also referred to as the cloud) can include servers, storage devices, networking devices, and/or other appropriate networked elements that provide cloud-based computing services. Data such as configuration, measurements, performance, etc. can be stored on devices 120 to be accessed later and/or further processed.

Figure 2:
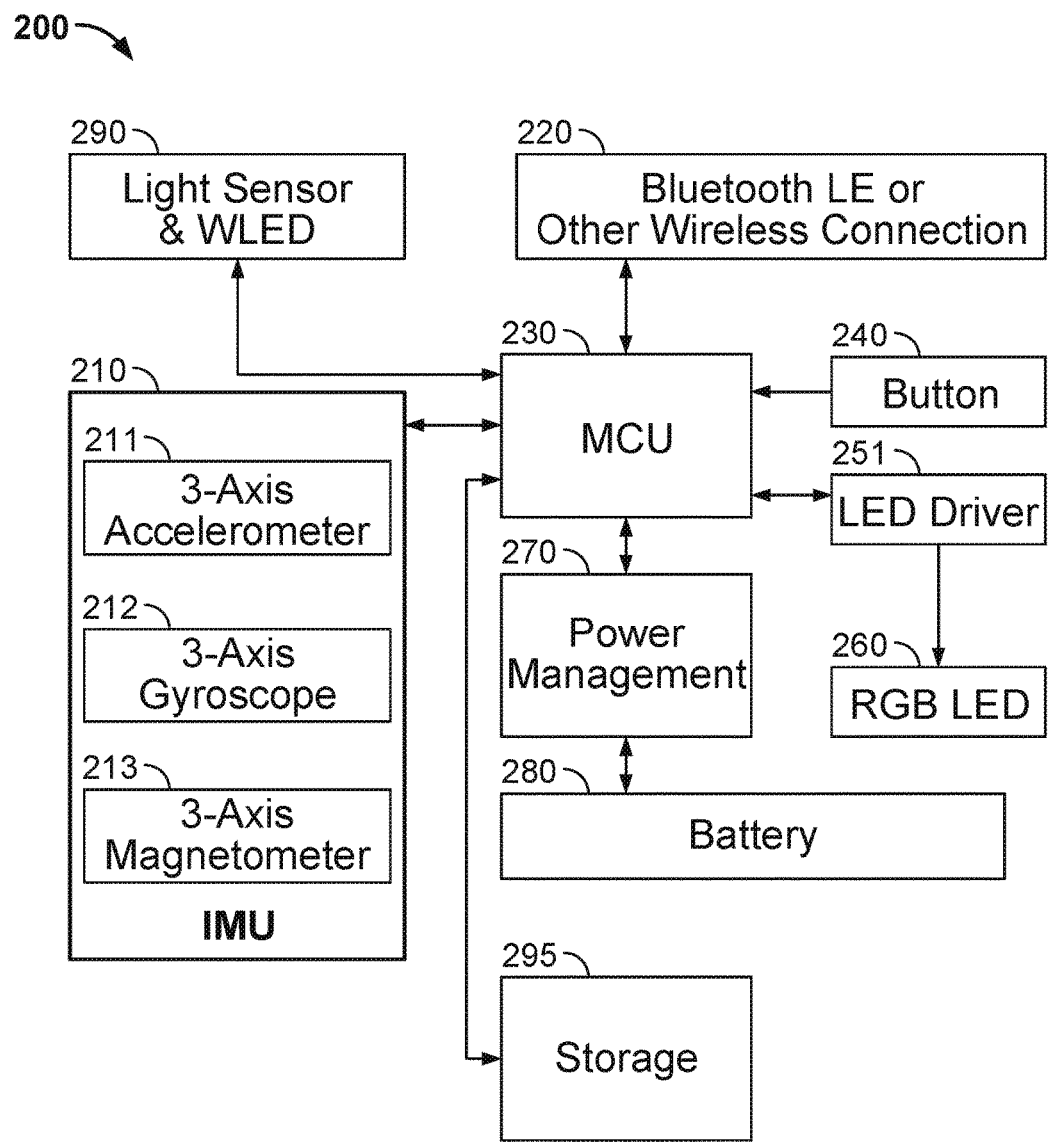
FIG. 2 is a block diagram illustrating an embodiment of a sensor device.

FIG. 2 is a block diagram illustrating an embodiment of a sensor device. In this example, sensor device 200 includes an inertial magnetic unit (IMU) 210 which includes a 3-axis accelerometer 211, a 3-axis gyroscope 212, and a 3-axis magnetometer 213. IMU 210 is connected with a microcontroller unit (MCU) 230. In this example, sample measurement data collected by the IMU is offloaded to a management device to be further processed. MCU 230 sends and receives data gathered by the IMU through a communication interface 220, which can be Bluetooth LE or other wireless connection, with a management device such as a smart phone, tablet, or PC. In other embodiments, the sensor device optionally includes a processor that processes the sample measurement data. A storage element 295 is connected to MCU 230. The storage element can be implemented using read-only memory (ROM), non-volatile random-access memory (NVRAM) (e.g., flash), nano-RAM, or any other appropriate devices.

Sensor device 200 includes an LED 260 controlled by LED driver 251, which is coupled both with the LED's hardware interface and with MCU 230. In some embodiments, LED 260 includes an RGB LED. The LED driver implements various control functions such as turning the LED on and off, switching color, changing intensity, etc. The MCU can invoke these control functions using an application programming interface (API) (e.g., function calls or commands) provided by the LED driver maker. In various embodiments, configuration information can be generated by MCU 230, or be generated by the management device which forwards the configuration information to the sensor device via communication interface 220. In response to the configuration information, the MCU invokes corresponding API calls and causes the LED driver to send appropriate control signals to LED 260 to configure the LED's on/off state, color, intensity, etc. In some embodiments, LED Driver 251 is incorporated into MCU 230.

The sensor device also optionally includes a button 240 (e.g., a push button or the like). In various embodiments, the button is multifunctional and can be used as a power on switch/sleep mode activator or a general purpose user interface button. The sensor device also optionally includes a light sensor and LED 290, which is configured to detect different types of mounting chassis on which the device is mounted. The sensor device 200 also includes a battery 280 or other appropriate power source. The voltage delivered to the other parts of the sensor device is delivered through power management module 270.

During the configuration phase, the user will assign a color and an identifier (name) to each sensor device he owns. In some embodiments, a management device such as a smartphone, a PC, a tablet, etc. is used to run the configuration application, which provides user interfaces through which the user may specify various configuration options. The configuration software installed on a management device (e.g., software that is installed on a smartphone, PC, tablet, etc.) is initiated. A sensor device connects to the management device via a wireless communication interface such as a Bluetooth interface. When the sensor device is activated, it sends an advertising message according to a predetermined protocol (e.g., a broadcast message formatted according to the Bluetooth LE protocol,) indicating that the sensor device is ready to connect to the management device. In some embodiments, the sensor device is configured with a unique identifier by the manufacturer, and the unique identifier is included in the advertising message.

Figure 3:
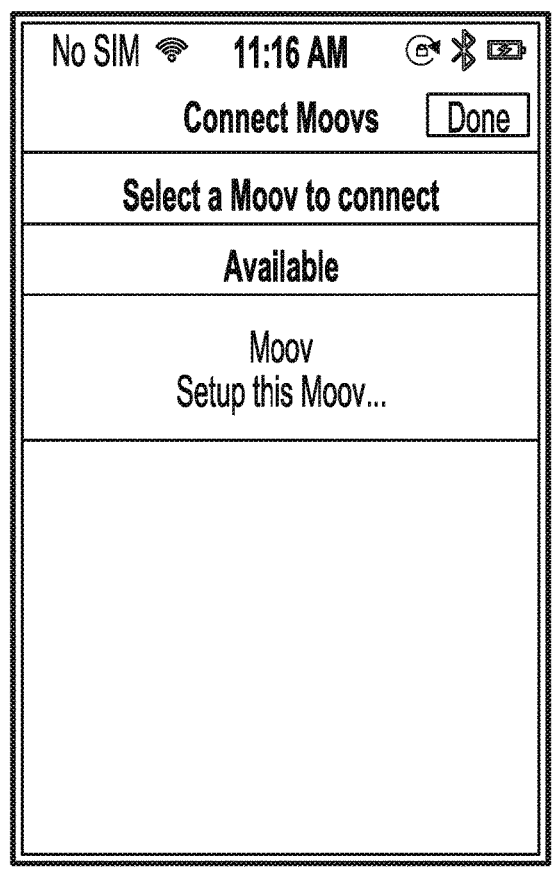
FIG. 3 is an example user interface screen showing an initialization screen where a new sensor device (with the default name of "Moov") is to be configured.

Upon receiving the message, the configuration application displays a user interface, notifying the user that the sensor device is ready to be configured. FIG. 3 is an example user interface screen showing an initialization screen where a new sensor device (with the default name of "Moov") is to be configured. The user may select the sensor device by its default name and proceed with configuration. When there are multiple devices, the configuration application will display a separate user interface screen for each sensor device for which a connection message is received.

Figure 4:
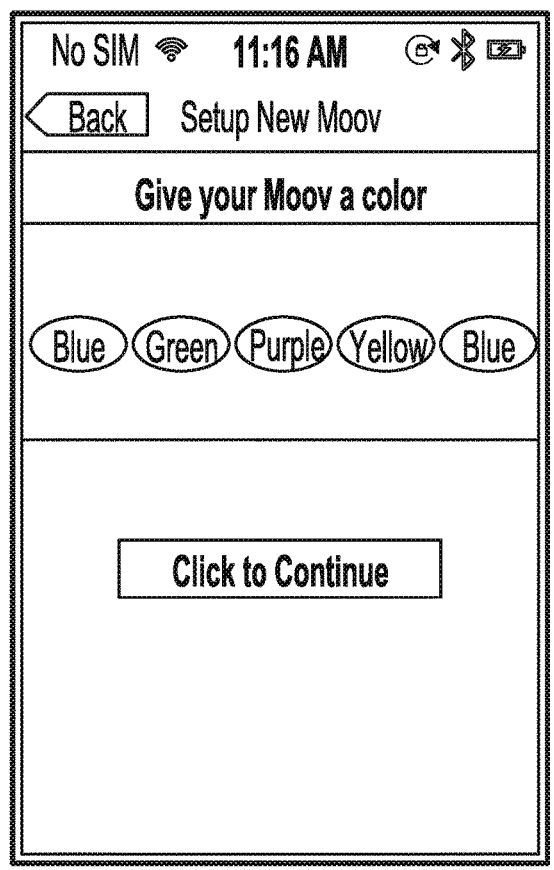
FIG. 4 is an example user interface screen of an embodiment of a configuration application showing a number of color choices the user may select from to assign a color to this sensor device.

In some embodiments, the sensor device includes an LED (e.g., an RGB LED) that is configurable to emit different colors of light depending on RGB values input into the LED's device interface. Thus, the configuration application requests the user to provide a color used to configure the sensor device's LED. FIG. 4 is an example user interface screen of an embodiment of a configuration application showing a number of color choices the user may select from to assign a color to this sensor device. The user can select any of the color choices; in some embodiments, the user can also specify a custom color other than the default color options by specifying a color code. The color code can be a standard color representation such as a set of RGB values or a custom color code (e.g., blue=1, green=2, purple=3, etc.). Other color code representations such as a set of HSL values, an HTML color code, etc., can also be used. The user can specify the color code directly, or select from a color wheel or chart showing additional color options. In some embodiments, an additional user interface (not shown) is provided for the user to enter an identifier for the sensor device.

The color specification and/or sensor identifier information entered by the user is sent by the management device to the sensor device via the communications interface between the devices (e.g., the Bluetooth interface), according to a predefined communication protocol. In some embodiments, a proprietary byte-based protocol format is used, where the message fields include identifier, action, data, etc. The possible values of the action field correspond to set, erase, reboot, etc. The possible values of the data field correspond to a color code. For example, the message format can be "sensor id=MyMoov123a, action=set, data=1." Other protocol formats can be used in other embodiments.

In some embodiments, the configuration application formats the configuration message comprising the sensor identifier, action, the color indication (which can be a color code or a command to set the LED to a specific color), etc., and invokes a custom protocol call to output the message via the management device's communication interface. In embodiments where the communication interface is Bluetooth, the custom protocol call can be implemented using the Bluetooth SDK. The message is transmitted to the sensor device's communication interface and further processed by the MCU. In response to receiving the configuration information, the MCU of the sensor device invokes appropriate API calls to the device driver to set the color according to the user's configuration, and causes a control signal to be sent to the LED. In response to the control signal, the LED will emit a color (e.g., blue) corresponding to the configuration. The configuration information is stored locally on the storage element of the sensor device.

In some embodiments, the management device further sends a message comprising the configuration information to a server (e.g., 120 of FIG. 1), which stores the configuration information in its local storage and optionally performs additional processing.

In some embodiments, instead of the user selecting from a set of pre-specified color choices by directly interacting with the management device (e.g., by touching the display screen of the management device with a finger if the management device has a touch screen, or by moving a mouse or other pointing device) via the user interface of FIG. 4, the user adjusts the orientation of the sensor device (e.g., by rotating the sensor device) to indirectly interact with the management device and change the color selection. As the user changes the orientation of the sensor device, the color selection changes both on the sensor device and on the user interface screen.

Figure 5:
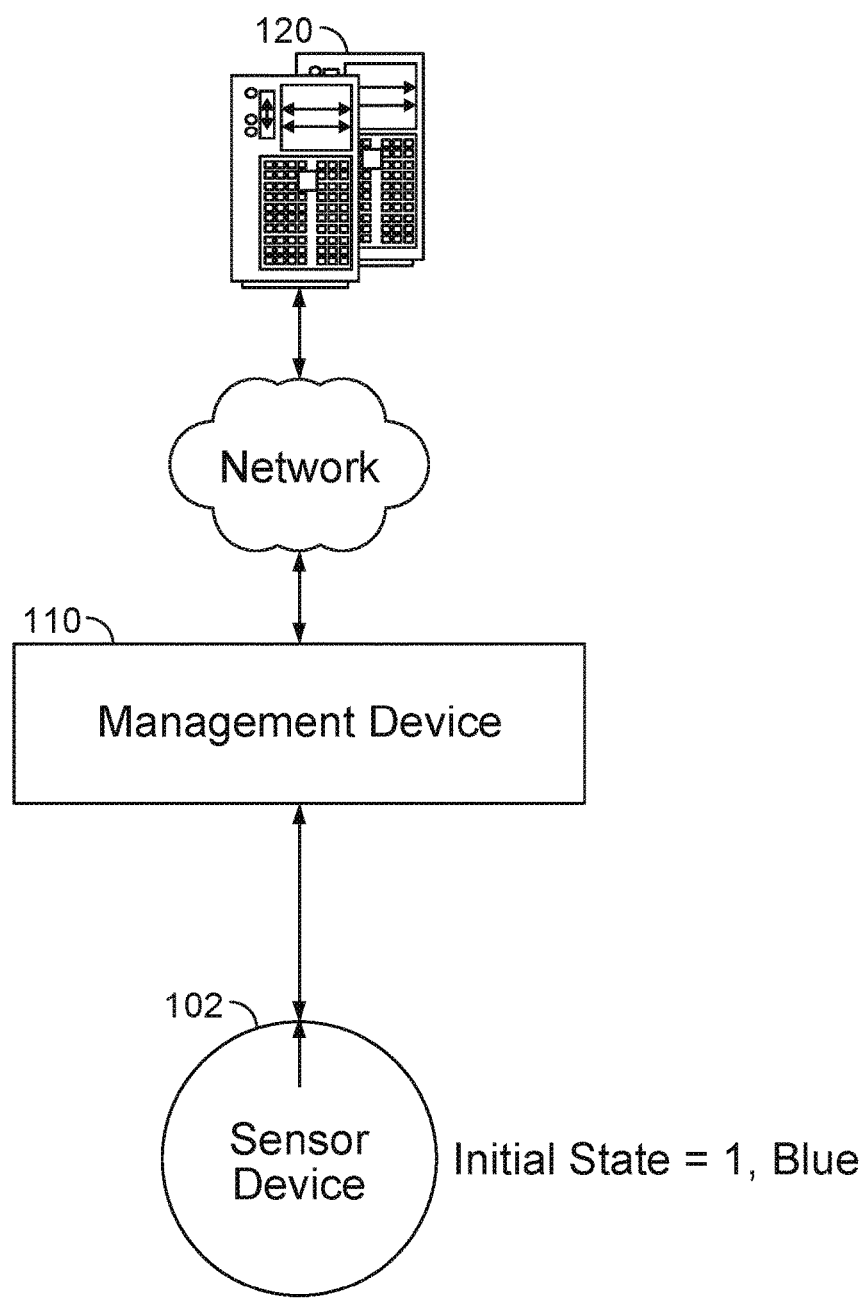
FIG. 5 is a diagram illustrating an example sensor device in its initial state.
Figure 6:
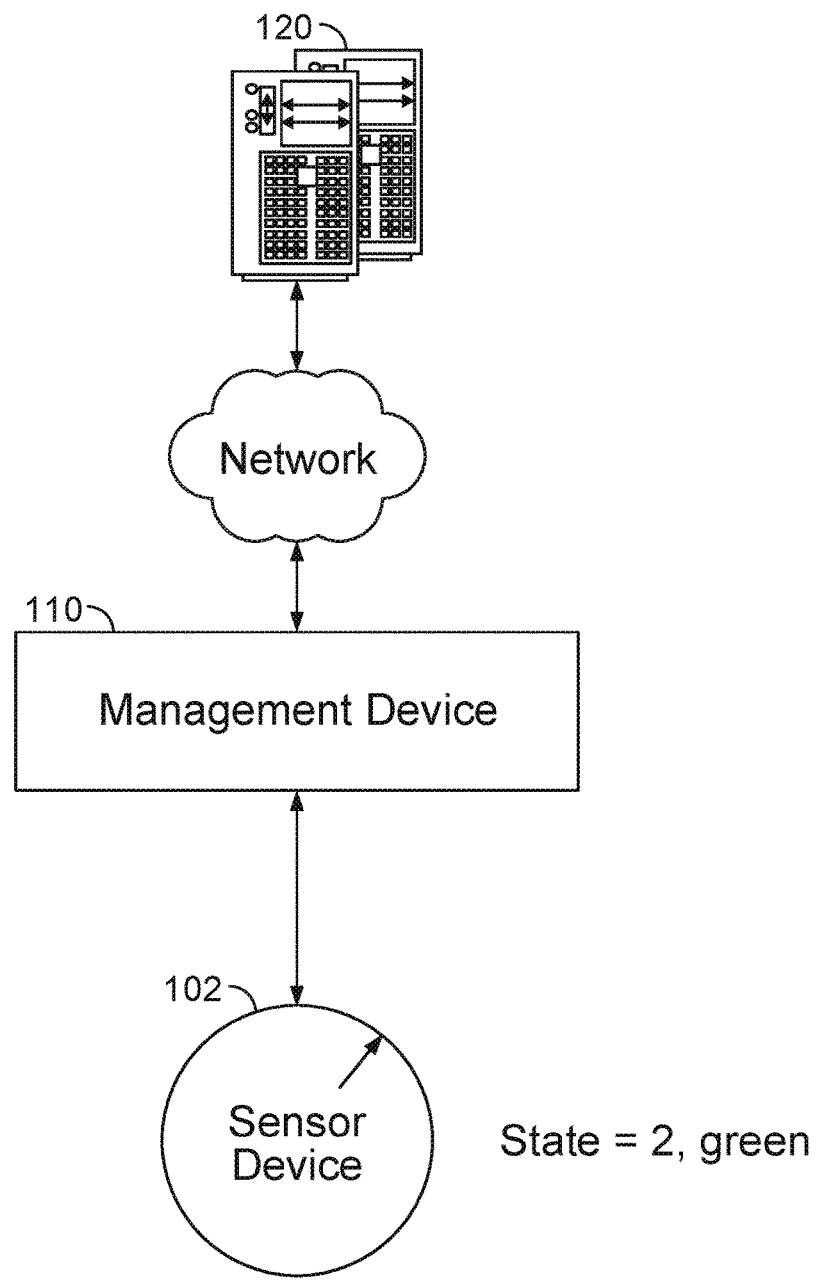
FIG. 6 is a diagram illustrating an example sensor device that has been rotated and put into a different state.

In particular, in some embodiments, there is a set of preconfigured mappings of states to color. In various embodiments, the mapping information can be stored on the sensor device and/or the management device. E.g., state 1=blue, state 2=green, state 3=purple, etc. FIG. 5 is a diagram illustrating an example sensor device in its initial state. Initially, the sensor device has an initial state/starting position and a corresponding initial color (e.g., state 1, blue), and the LED is configured to emit light in the initial color. When the user rotates the sensor device, the sensors within the sensor device will detect the amount of rotation relative to the initial starting position. If the amount of rotation exceeds a threshold (e.g., 45 degrees relative to the initial starting position), then the state will advance to the next state, and the color selection will change to the corresponding color of the next state. For example, to state 2, green. FIG. 6 is a diagram illustrating an example sensor device that has been rotated and put into a different state.

In some embodiments, the MCU has low processing power; thus, each time the sensor is rotated, the raw measurement data from the IMU is communicated from the sensor device to the management device according to a pre-specified protocol. The management device computes the orientation, state, and/or color information, and sends a set color message back to the sensor device to configure the LED color. The management device further updates the configuration application to display a color that matches the color set on the sensor device. The orientation, state, and/or color information is stored on the management device.

In some embodiments, the MCU has sufficient processing power to compute the orientation, state, and color information. Thus, the state/color computation is performed on the sensor device locally, the LED color is reset according to the results, and the results (e.g., orientation, state, and/or color information) are sent to the management device according to a pre-specified protocol. Upon receiving the results, the management device updates the configuration application to display a matching color.

After the sensor is rotated and its color updated, the starting position of the sensor device is reset to its current position. If the user continues to rotate the sensor device and the amount of rotation relative to the new starting position exceeds the threshold, the state will advance again (e.g., to state 3, purple). In some embodiments, the color state switches in a predetermined order (e.g., state 1 to state 2 to state 3 and so on) as long as the absolute value of the position change exceeds the threshold. In some embodiments, the color state change matches the relative orientation change of the sensor device; for example, if the sensor device is rotated clockwise by 45 degrees or more, the color changes from state 2, green to state 3, purple, but if the sensor device is rotated counterclockwise by 45 degrees or more, the color changes from state 2, green to state 1, blue.

Processing Techniques

Color Configuration

In some embodiments, the orientation of the device is represented using a quaternion Q. At each sample point, an interpolated and corrected current quaternion Q(n) is computed using sensor data. An angle between the current quaternion Q(n) and the initial quaternion Q(0) is further computed. A mapping of angular ranges to colors is used to determine the color that corresponds to the angle, and to configure the LED on the sensor device to the corresponding color.

Figure 7:
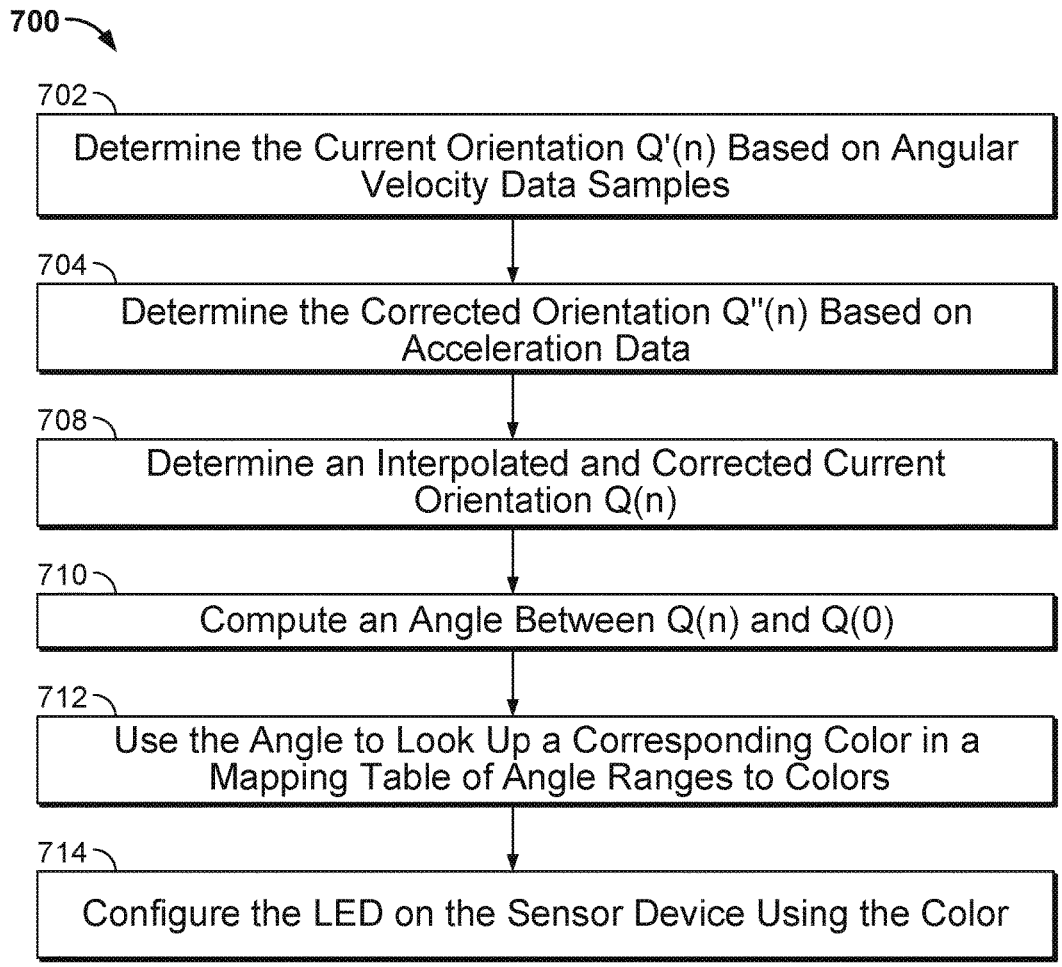
FIG. 7 is a flowchart illustrating an embodiment of a process for configuring device color based on the orientation of the device.

FIG. 7 is a flowchart illustrating an embodiment of a process for configuring device color based on the orientation of the device. Process 700 can be performed by the management device or by the sensor device.

The initial quaternion Q(0) corresponds to the initial orientation of the device at the beginning of the configuration.

The sensors sample data at a sampling rate (e.g., 1 set of data samples every 0.5 seconds), and the sensor outputs are used to compute Q(n) for the n-th sample. In some embodiments, the sensors are calibrated and initialized by a pre-processor. For example, the sensors can have offsets due to imperfections in their hardware. An initial calibration process adjusts for such offsets and errors. In some embodiments, the initial calibration process is performed by the manufacturer of the sensor device. A set of calibration functions with certain calibration parameters is applied to the raw sensor outputs A, G, and M to obtain calibrated and initialized outputs Ai, Gi, and Mi as follows:

$$Ai = \text{calibration}_{Ai}(A, \text{calibration\_parameters}) \quad (1)$$

$$Gi = \text{calibration}_{G}(G, \text{calibration\_parameters}) \quad (2)$$

$$Mi = \text{calibration}_{Mi}(M, \text{calibration\_parameters}) \quad (3)$$

The actual calibration functions and calibration parameters are determined empirically and may vary in different implementations. For example, the calibration function can subtract certain offsets from a raw output, multiply the raw output by a constant, etc.

Corrected orientation data is determined based at least in part on the angular velocity data, the acceleration data, and the magnetic field data if available. Preferably, preprocessed data based on the raw measurements is used. At 702, the current orientation (of the current sample n) is determined based at least in part on the angular velocity data samples (gyroscope reading Gi), which has a linear relationship to local space rotational velocity Ro. In this example, Gi is the same as Ro, although other linear relationships may exist between the two in other embodiments. Specifically, the current orientation data sample (expressed as the quaternion Q'(n), n being the sample index or time index) is updated by performing a quaternion transform operation on the previous interpolated orientation data sample Q(n−1) and the current local space rotational velocity Ro(n) as follows:

$$Q'(n) = \text{transform}_Q(Q(n-1), Ro(n), \text{time\_step}) \quad (4)$$

where $\text{transform}_Q$ is a standard quaternion transform function.

If left uncorrected, the output Q'(n) will drift over time. Thus, at 704, a corrected orientation Q"(n) is determined based at least in part on the acceleration data samples. Particular, the preprocessed acceleration data Ai and the preprocessed magnetic field data Mi are used in the determination. Specifically, Ai and Mi form a local coordinate system relative to the world coordinate system. The local coordinate system is a coordinate system that is relative to the device itself. The rotational transform of the world space to the local coordinate system is expressed as Q"(n) and derived as follows:

First, a 3×3 rotational matrix Mr is constructed from Ai and Mi, where $$\text{vec3}Y = \text{normalize}(Vec3::\text{Cross}(Mi, Ai)); \quad (5a)$$

$$\text{vec3}X = \text{normalize}(Mi); \quad (5b)$$

$$\text{vec3}Z = \text{normalize}(Ai); \quad (5c)$$

$$Mr.\text{column1}.x = X.x; \quad (5d)$$

$$Mr.\text{column1}.y = Y.x; \quad (5e)$$

$$Mr.\text{column1}.z = Z.x; \quad (5f)$$

$$Mr.\text{column2}.x = X.y; \quad (5g)$$

$$Mr.\text{column2}.y = Y.y; \quad (5h)$$

$$Mr.\text{column2}.z = Z.y; \quad (5i)$$

$$Mr.\text{column3}.x = X.z; \quad (5j)$$

$$Mr.\text{column3}.y = Y.z; \quad (5k)$$

$$Mr.\text{column3}.z = Z.z; \quad (5l)$$

Then, rotational matrix Mr is then converted to a quaternion Q"(n) using a standard mathematical transform.

At 708, an interpolated and corrected current orientation Q(n) is determined by interpolating Q'(n) and Q"(n). Any known interpolation function can be used. In some embodiments, a weighted linear interpolation function is used as follows:

$$Q(n) = \text{interpolate}(Q'(n), Q"(n), \text{alpha}) \quad (6)$$

Typically, 0<alpha<1. The weight alpha is based on the stableness of the raw sensor reading. The more stable the reading is, the greater the weight assigned to Q"(n). In some embodiments, the stability of the sensor reading is determined based on a probability distribution. A more concentrated probability distribution indicates greater stability and corresponds to a greater weight.

At 710, the angle between the interpolated and corrected current orientation Q(n) and the initial orientation Q(0) is computed according to the standard technique for computing an angle between two vectors. The resulting angle is a scalar value.

In this example, a mapping of angle ranges and colors is predefined and stored in a mapping table. For example, the angle range of [0-45°) maps to the color blue, the angle range of [45°-90°) maps to the color green, etc. Thus, at 712, using the angle that is determined and the angle range in which the computed angle falls, the corresponding color is looked up in the mapping table.

At 714, the LED on the sensor device is configured using the corresponding color. In some embodiments, the color configuration is sent to the sensor device via the communication interface, and the sensor device's MCU processes the information that is received, and invokes a control function with respect to the LED driver to set the color to the one that is found to correspond to the computed angle.

Additional Processing

The raw measurement data can also be processed to determine form data associated with the user's performance during exercises. That is, raw measurement data is collected during exercises and form data such as acceleration is determined. In some embodiments, the process performs 702-710 of process 700 to compute the interpolated and corrected current orientation Q(n). Subsequently, in some embodiments, the corrected velocity is determined based at least in part on Q(n) and a statistical model. An acceleration in world space, Aw(n), is determined. Since the accelerometer reading includes the earth's gravity, the transform function transforms the acceleration reading in world space Ai(n) based on the estimated orientation, and then removes gravity from the transformed value to determine the acceleration in world space as follows:

$$Aw(n) = \text{transform}_v(Ai(n), Q(n)) - \text{gravity} \quad (7)$$

where transform is a standard vector transform that transforms Ai to a new direction according to Q.

In some embodiments, the acceleration is integrated to determine a current velocity V(n) as follows:

$$V(n) = V(n-1) + Aw(n) * \text{time\_step} \quad (8)$$

If left uncorrected, velocity V(n) will drift over time. Thus, a statistical model is used to remove the accelerometer's bias or zero offset, and minimize errors in velocity estimation.

In some embodiments, the statistical model is a distribution model of sensor output features to ground truth human motion velocity. The motion data of various human users wearing various sensors and performing exercises is captured using a system that is independent of the sensors and that is known to produce accurate measurements. For example, a camera-based system is used in some embodiments to capture sample position data of the users' leg movements. Multiple position data can be captured for a single action such as a single step. To build the model, sample data of many steps taken by many different users wearing different sensors is captured. The sample position data may be further processed to accurately derive other data such as velocity associated with these motions. In particular, the velocity that is determined using the independent system is referred to as "ground truth velocity." Meanwhile, the sensors also capture data, and a set of sensor output features derived based on the sensors' outputs is determined. Examples of the sensor output features include the statistical variance, frequency, and magnitude of the captured sensor data. The features characterize the motions being performed. For example, a slow motion tends to correspond to a low variance in the sensor output data, and a fast motion tends to correspond to a high variance in the sensor output data.

In some embodiments, a probability distribution of the ground truth velocity for a specific sensor output feature is determined based on a statistical model for the given sensor output feature. Examples of a sensor output feature include frequency, variance, standard deviation, and any other appropriate characteristics derived from the acceleration data, the angular velocity data, and/or magnetic field data. In some embodiments, the sensor output feature is a vector in multiple dimensions where each dimension corresponds to a particular feature of a particular type of sensor output (e.g., the frequency for acceleration data). The probability distribution function is expressed as P (Vg, sensor_feature).

Figure 8:
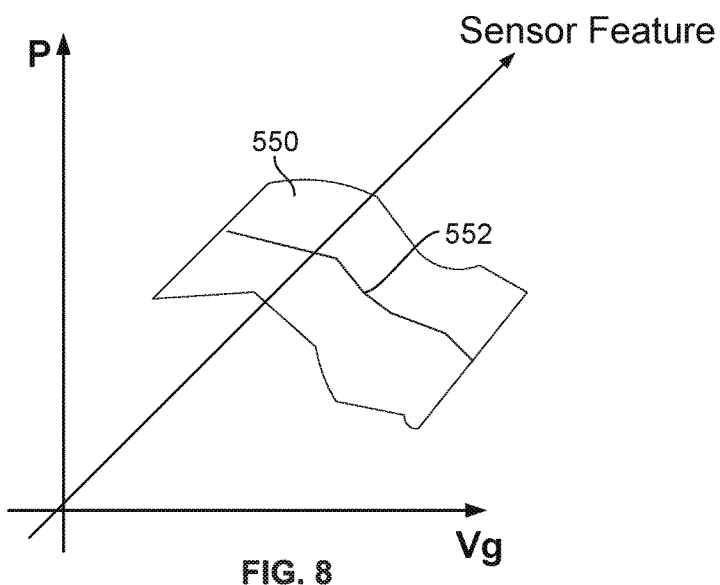
FIG. 8 illustrates an example statistical model of ground truth velocities relative to a specific sensor output feature in a single dimension.

FIG. 8 illustrates an example statistical model of ground truth velocities relative to a specific sensor output feature in a single dimension. In this example, the sensor output feature corresponds to the frequency of one set of sensor measurement data (e.g., as determined by performing an operation such as a Fourier transform on the sensor measurement). Other sensor output features such as variance, standard deviation, etc., can be used and correspond to different statistical distribution functions. Specifically, the statistical model in this example is represented as a 3-D surface 550 that corresponds to a function P (Vg, sensor_feature). Given this distribution function, for a given frequency, there is a corresponding probability distribution of ground truth velocities (e.g., function curve 552). Accordingly, for each sample point, there is a corresponding sensor output feature value, and a corresponding distribution of possible human velocity, expressed as $P_x'$ (Vg), where x is the sample index. Further, given the probability distribution P, there is a corresponding preset alpha that is set based on how stable the distribution is, which is used in the interpolation function (6).

Returning to the data processing process, in some embodiments, an offset of the velocity is determined such that the sum of probabilities for n over a sample window of (n0, n1) is maximized, as follows:

$$\text{Maximize}(\Sigma_{n=n0}^{n1} P_n'(V(n)-\text{Voff}(n))) \qquad (9)$$

where Voff(n)=a*n+b, where n is the sample index or time. An optimization algorithm such as a search-based optimization or any other appropriate optimization algorithm is used to solve for a and b to maximize the sum of the corrected probability values over the window n0 and n1. The window size is preferably set to the average time for a typical user to perform a motion (e.g., if it takes on average 0.5 seconds to perform a motion and the sample rate is 100 samples/second, then the window size is preferably set to 0.5*100=50 samples).

In some embodiments, the corrected current output velocity V"(n) is capped based on the current output feature's distribution at the current sample point and the offset is as follows:

$$V''(n)=\text{Normalize}(V'(n))*\text{Min}(\text{magnitude}(V'(n)), V\text{max\_magnitude}(n))) \qquad (10)$$

where V'(n)=V(n)−Voff, Vmax_magnitude(n) is the maximum velocity the motion can reach based on the current sensor output features with a certain degree of confidence or probability. For example, it is 99% likely that the user cannot reach more than two meters per second with this motion pattern.

Although the example process above includes a magnetometer measurement, the magnetometer measurement is optional. A coordinate system can still be built without the magnetometer measurement, even though information about the North direction is lost and the horizontal direction cannot be determined. In practice, the coaching system can still give the user feedback on his form by arbitrarily selecting a north direction.

The automated fitness coaching system is often implemented in a lossy environment where some samples transmitted from the sensor device to the management device can be lost. An index-based transmission technique is implemented in some embodiments to make corrections in the event of data loss. In some embodiments, each set of sensor outputs (A, G, and optionally M) is transmitted with a sample index that increments from an initial value to a maximum value (e.g., from 0 to 255) then resets to the initial value, so that the receiver (e.g., the management device) can track and repair lost packets or samples. If one or more samples are lost, the sample points are interpolated based on the samples before and after the lost ones such as the following:

$$S(\text{lost})=\text{Interpolate}(S(\text{lost}-1),S(\text{lost}+1),0.5) \qquad (11)$$

The above example interpolation function is a linear interpolation function. Different interpolation techniques can be used in other embodiments.

In some embodiments, the management device is installed with different applications for different types of exercises. The user may select an appropriate application for the specific exercise he is doing. The application determines, based on sensor measurements and using a process such as what is described above, corrected core measurements for velocity, orientation, etc. In some embodiments, the corrected core measurements are further processed to derive additional corrected core measurements (e.g., acceleration) and/or additional form measurements such as cadence, range of motion, landing impact, etc. Details of the specific applications are outside the scope of this application.

Identifier Configuration

In some embodiments, device information including configuration information, measurement data collected during exercise sessions, etc. is stored on the cloud (e.g., on a database server 120 of FIG. 1). Typically, the sensor device has a unique device identifier that is assigned by the device manufacturer. In some embodiments, the device identifier is directly accessible by the management device (e.g., through an operating system-supported API call such as getDeviceID). Thus, in such cases, this device identifier can be used as an index for storing and looking up the device information in a database. In some cases, however, the device identifier cannot be directly accessed by the management device. For example, on certain operating systems such as iOS®, due to data security concerns, when an API call is made to obtain the device identifier, the operating system will obfuscate the device identifier. Thus, different management devices may return different obfuscated device identifiers for the same sensor device. For example, suppose that a sensor device has a device manufacturer specified device identifier "M123." When the sensor device is connected to a first iOS® management device such as an iPhone, an operating system-supported API call made by the management device to get the device identifier will return an obfuscated device identifier "KH823." When the sensor device is connected to a second iOS® management device such as an iPad, the same API call will return a different obfuscated device identifier "UWE47." Thus, the device identifier that is returned by the operating system-supported API cannot be easily used as the index for saving or storing the device information and another solution is needed.

Figure 9:
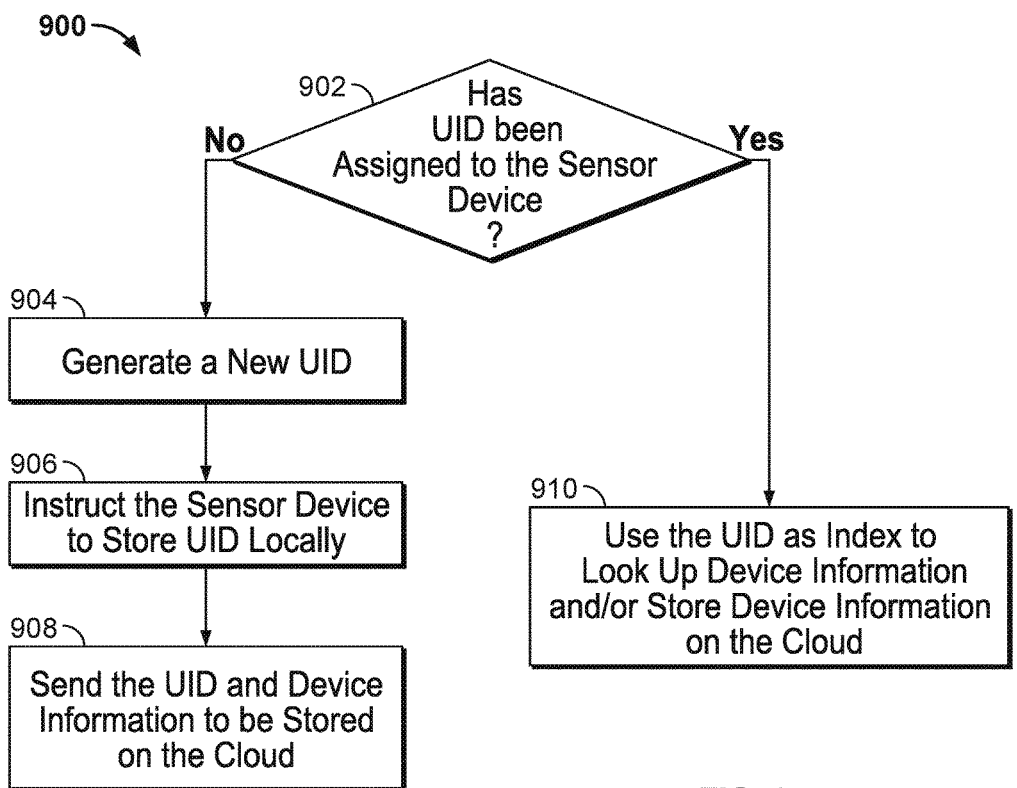
FIG. 9 is an embodiment of a process for generating and using the UID.

In some embodiments, rather than relying on the operating system-supported API to return the manufacturer assigned device identifier, another unique identifier (also referred to as the UID) is generated, assigned to the sensor device, and used to store device data. FIG. 9 is an embodiment of a process for generating and using the UID. Process 900 can be performed by the management device.

Process 900 initiates when the sensor device is activated. At 902, the management device will query the sensor device to determine whether the UID has been assigned. In some embodiments, the query is implemented by a custom function (rather than the operating system-supported get device identifier API) that makes a call to the sensor device to check a local storage for the UID. If no UID is found, at 904, a new UID is generated. There are a variety of techniques for generating the UID. For example, a serial number generator can be used to generate the UID by incrementing and returning a counter value each time the serial number generator is called. As another example, the UID can have the same value as the manufacturer assigned device identifier (if the latter is guaranteed to be unique). As another example a standard UUID generation function is invoked to generate the UID.

At 906, the management device instructs the sensor device to store the UID locally. Further, at 908, the management device sends the UID as well as the device information to be stored on the cloud (e.g., server 120). In some embodiments, the UID is used as the index for saving the device information in a database on the cloud.

If, however, at 902, it is determined that a UID has been assigned, then the management device can be used to configure the sensor device and collect data as usual. At 910, the UID is used as the index into the device information database to look up the corresponding device information and/or store device information such as newly collected measurement data, performance data, etc., as appropriate. This way, the same sensor device is recognized by different management devices as the same device, and existing configuration information and application data can be displayed even if a different management device is used.

In some embodiments, rather than assigning a UID as described in process 900, there is a custom protocol established between the sensor device and the management device to allow the devices to directly communicate data such as byte-formatted data. In some embodiments, the custom protocol is built on top of the iOS Bluetooth SDK functions (e.g., functions used to send data packets). The sensor device retrieves its device identifier, puts the identifier in the payload of a packet, and sends the packet to the management application according to the protocol. This way, the management device can obtain the device identifier without relying on the operating system-supported API call that obfuscates the device identifier.

Configuration of an automated personal fitness coaching device has been described. The configuration process is intuitive and allows the user to distinguish between multiple devices as well as manage the devices using multiple management devices.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A device, comprising:
   a light emitting diode (LED);
   a set of one or more sensors configured to obtain motion data samples; and
   one or more processors coupled to the LED and the set of one or more sensors, wherein:
   a color configuration is determined based at least in part on a rotation associated with the device, the rotation being determined based at least in part on the motion data samples; and
   the one or more processors are configured to:
   obtain an indication of the color configuration; and
   cause a control signal to be sent to the LED to cause the LED to emit a color according to the color configuration.

2. The device of claim 1, further comprising a communication interface configured to receive the indication of the color configuration from a management device.

3. The device of claim 1, further comprising a communication interface configured to send a device identifier to a management device according to a custom protocol.

4. The device of claim 1, wherein the color configuration is obtained based at least in part on the motion data samples.

5. The device of claim 1, wherein the color configuration corresponds to an amount of orientation associated with the device.

6. The device of claim 1, wherein the motion data samples are used to determine an amount of rotation associated with the device by:
   determining a current orientation based on angular velocity data samples;
   determining a corrected orientation based on acceleration data samples; and
   determining an interpolated and corrected current orientation.

7. The device of claim 5, wherein:
   the motion data samples are used to determine an amount of rotation associated with the device by:
   determining a current orientation based on angular velocity data samples;
   determining a corrected orientation based on acceleration data samples; and
   determining an interpolated and corrected current orientation; and
   the color configuration corresponding to the amount of orientation is determined by:
   determining an angle between the interpolated and corrected current orientation and an initial orientation; and
   looking up in a mapping of angle ranges to colors a color that corresponds to the determined angle.

8. The device of claim 1, wherein the one or more processors are configured to compute an amount of rotation associated with the device and determine the indication of the color configuration based at least in part on the amount of rotation associated with the device.

9. The device of claim 1, further comprising a storage; and wherein configuration information pertaining to the indication of the color configuration associated with the device is saved to the storage.

10. The device of claim 1, further comprising a local storage configured to store a unique identifier (UID), and wherein the UID is further stored on a network storage.

11. A device, comprising:
a light emitting diode (LED);
a set of one or more sensors configured to obtain motion data samples;
a communication interface configured to:
send at least a portion of the motion data samples to a management device to cause the management device to determine indication of a color configuration based at least in part on an amount of rotation associated with the device; and
receive the indication of the color configuration from the management device; and
one or more processors coupled to the LED, the set of one or more sensors, and the communication interface, wherein
the one or more processors are configured to:
obtain an indication of the color configuration; and
cause a control signal to be sent to the LED to cause the LED to emit a color according to the color configuration.

12. A method, comprising:
obtaining a plurality of motion data samples;
obtaining an indication of a color configuration, the color configuration being determined based at least in part on the plurality of motion data samples; and
sending a control signal to a light emitting diode (LED) to cause the LED to emit a color according to the color configuration, wherein
the color configuration is determined based at least in part on a rotation associated with a device, the rotation being determined based at least in part on the plurality of motion data samples.

13. The method of claim 12, wherein the indication of the color configuration is received from a management device.

14. The method of claim 12, further comprising sending a device identifier to a management device according to a custom protocol.

15. The method of claim 12, wherein the color configuration is obtained based at least in part on the motion data samples.

16. The method of claim 12, wherein the color configuration corresponds to an amount of orientation associated with the device.

17. The method of claim 12, wherein the plurality of motion data samples are used to determine an amount of rotation associated with the device by:
determining a current orientation based on angular velocity data samples;
determining a corrected orientation based on acceleration data samples; and
determining an interpolated and corrected current orientation.

18. The method of claim 16, wherein:
the motion data samples are used to determine an amount of rotation associated with the device by:
determining a current orientation based on angular velocity data samples;
determining a corrected orientation based on acceleration data samples; and
determining an interpolated and corrected current orientation; and
the color configuration corresponding to the amount of orientation is determined by:
determining an angle between the interpolated and current orientation and an initial orientation; and
looking up in a mapping of angle ranges to colors a color that corresponds to the determined angle.

19. The method of claim 12, further comprising computing an amount of rotation associated with the device and determining the indication of the color configuration based at least in part on the amount of rotation associated with the device.

20. The method of claim 12, further comprising storing information pertaining to the indication of the color configuration associated with the device to a local storage.

21. The method of claim 12, further comprising:
obtaining a unique identifier (UID);
storing the UID locally; and
causing the UID to be stored on a network.

22. A method, comprising:
obtaining a plurality of motion data samples;
obtaining an indication of a color configuration, the color configuration being determined based at least in part on the plurality of motion data samples, including:
sending at least a portion of the motion data samples to a management device to cause the management device to determine the indication of the color configuration based at least in part on an amount of rotation associated with a device;
receiving the indication of the color configuration from the management device; and
sending a control signal to a light emitting diode (LED) to cause the LED to emit a color according to the color configuration.

23. A computer program product embodied in a tangible non-transitory computer readable storage medium and comprising computer instructions for:
obtaining a plurality of motion data samples;
obtaining an indication of a color configuration, the color configuration being determined based at least in part on a rotation associated with a device, the rotation being determined based at least in part on the plurality of motion data samples; and
sending a control signal to a light emitting diode (LED) to cause the LED to emit a color according to the color configuration.

* * * * *

UNITED STATES PATENT AND TRADEMARK OFFICE
CERTIFICATE OF CORRECTION

PATENT NO. : 9,699,859 B1  
APPLICATION NO. : 14/814092  
DATED : July 4, 2017  
INVENTOR(S) : Li et al.

Page 1 of 1

It is certified that error appears in the above-identified patent and that said Letters Patent is hereby corrected as shown below:

In the Specification

In Column 5, Line 07, after "sensor id =", delete "MyMoov123a" and insert --MyMoov123--, therefor.

In Column 6, Line 65, delete "Gi = calibrationG(G,calibration_parameters)", and insert --Gi = calibrationGi(G,calibration_parameters)--, therefor.

In Column 9, Line 46, delete "Maximize($\sum_{n=n0}^{n1} P_n'(V(n)-Voff(n))$)" and insert -- $Maximize(\sum_{n=n0}^{n1} P_n'(V(n) - Voff(n)))$ --, therefor.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*